United States Patent [19]

Shih

[11] Patent Number: 5,720,612
[45] Date of Patent: Feb. 24, 1998

[54] METHOD AND APPARATUS OF RECORDING AND REPRODUCING THE PATH OF INSERTION OF A CAST ON SURVEYORS

[76] Inventor: Jui-Yuan Shih, No. 79, Min Tsu Rd., Lu Kang Chen, Changhua Hsien, Taiwan

[21] Appl. No.: 564,432

[22] Filed: Nov. 29, 1995

[51] Int. Cl.$^6$ .................................................. A61C 11/00
[52] U.S. Cl. ............................................ 433/55; 433/57
[58] Field of Search ................................ 433/54, 57, 60, 433/61, 62, 63, 55

[56] References Cited

U.S. PATENT DOCUMENTS

| | | | |
|---|---|---|---|
| 5,026,282 | 6/1991 | Koike | 433/62 |
| 5,073,109 | 12/1991 | El Hadary | 433/61 X |
| 5,266,029 | 11/1993 | Feber | 433/61 |
| 5,482,460 | 1/1996 | Farnor, Jr. et al. | 433/57 |

*Primary Examiner*—Nicholas D. Lucchesi
*Attorney, Agent, or Firm*—Bacon & Thomas

[57] ABSTRACT

A method an apparatus for recording and reproducing the path of insertion of a cast on a dental surveyor uses an iterative method to enable rapid equalization of the height of three points on the cast by first rotating the table on which the cast is situated about a spindle supported by two mutually perpendicular pivotal adjustment arms so that a line connecting two of the points a,b is as close as possible to being parallel with a long axis of a generally horizontal one of the pivotal adjustment arms, pivoting the horizontal adjustment arm so that points a,b are at an equal height, pivoting the generally vertical adjustment arm so that point a and a third point c are at an equal height, readjusting the horizontal adjustment arm so that points a and b are again at an equal height, readjusting the vertical adjustment arm so that points a and c are again at an equal height, and so forth until all three points are at the same height.

3 Claims, 9 Drawing Sheets

METHOD AND APPARATUS OF RECORDING AND REPRODUCING THE PATH OF INSERTION OF A CAST ON SURVEYORS

CROSS-REFERENCE TO RELATED APPLICATION

This application is further improvement on a U.S. patent application Ser. No. 08/372,324 now pending.

BACKGROUND OF THE INVENTION

The present invention relates to a method and an apparatus of recording and reproducing the path of insertion of a cast on a dental surveyor, and more particularly to an "iteration method" developed according to the principle of similar triangles in geometry. By means of the iteration method, the three dots on the cast are quickly adjusted to be on an identical level with minimized error.

Several methods have been disclosed in the dental field for recording and reproducing the path of insertion of a cast on a dental surveyor, including the scoring method or tripod-marks method. In the aforesaid original application, the applicant provides an easy and efficient method of recording and reproducing the path of insertion of a cast on a dental surveyor and an adjustable surveyor table used in the method so as to more accurately and quickly determine a cast position without trial and error.

However, it has been found by the applicant that although the method and apparatus disclosed in the original application are greatly advantageous over the prior art, it is still somewhat troublesome to make the three dots a, b, c on an identical level. Therefore, the inventor has developed another "interapproaching method" which uses the principle of similar triangles to further facilitate the procedure of recording and reproducing the path of insertion of a cast on a dental surveyor.

Figure 2:
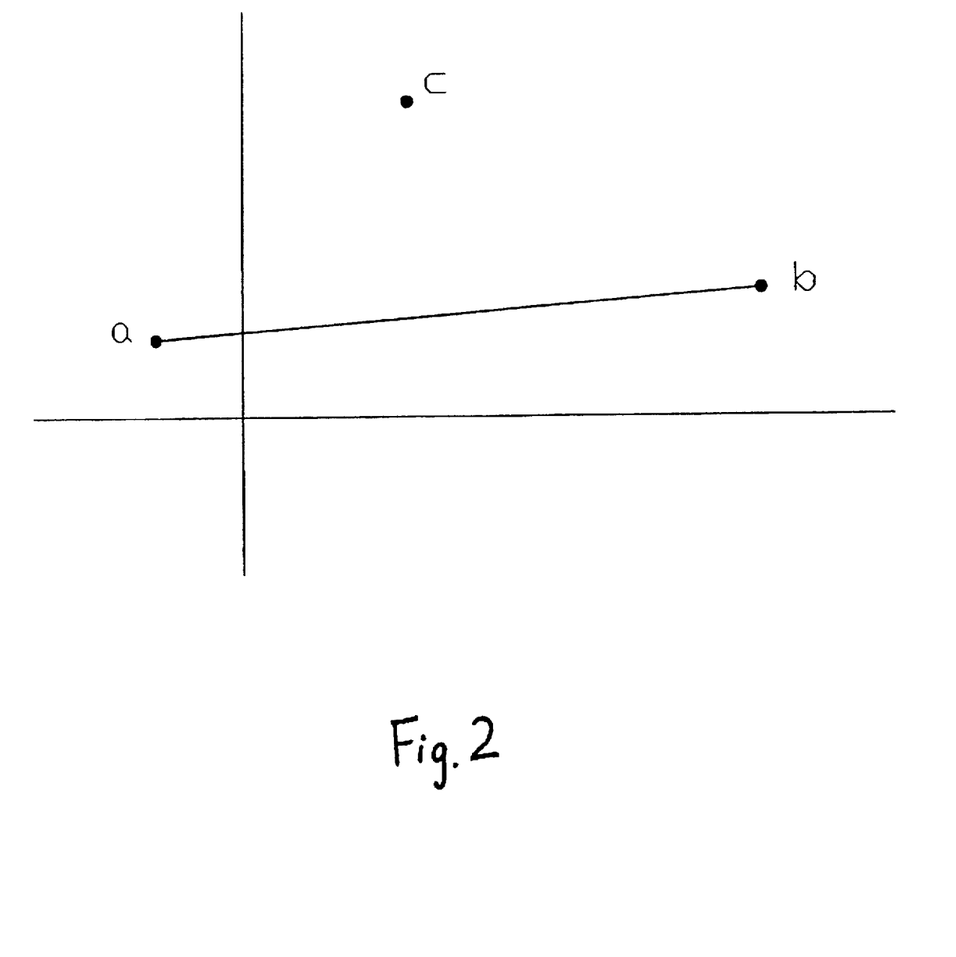
FIG. 2 is a view of the projections of the three points on plane H, illustrating the principle of similar triangles utilized by the present invention.

The principle underlying the present invention is illustrated as follows:

Please refer to FIG. 2 which is a view of the projections of the three points on plane H. The transverse axis in FIG. 2 is the projection of the long axis of the lower joint, while the longitudinal axis is the projection of the upper joint. In FIG. 2, points a, b are at equal height and the line created by points a, b is nearly parallel to the long axis of the lower joint. At this time, point c is higher than points a, b with a height difference of Hc.

Figure 3:
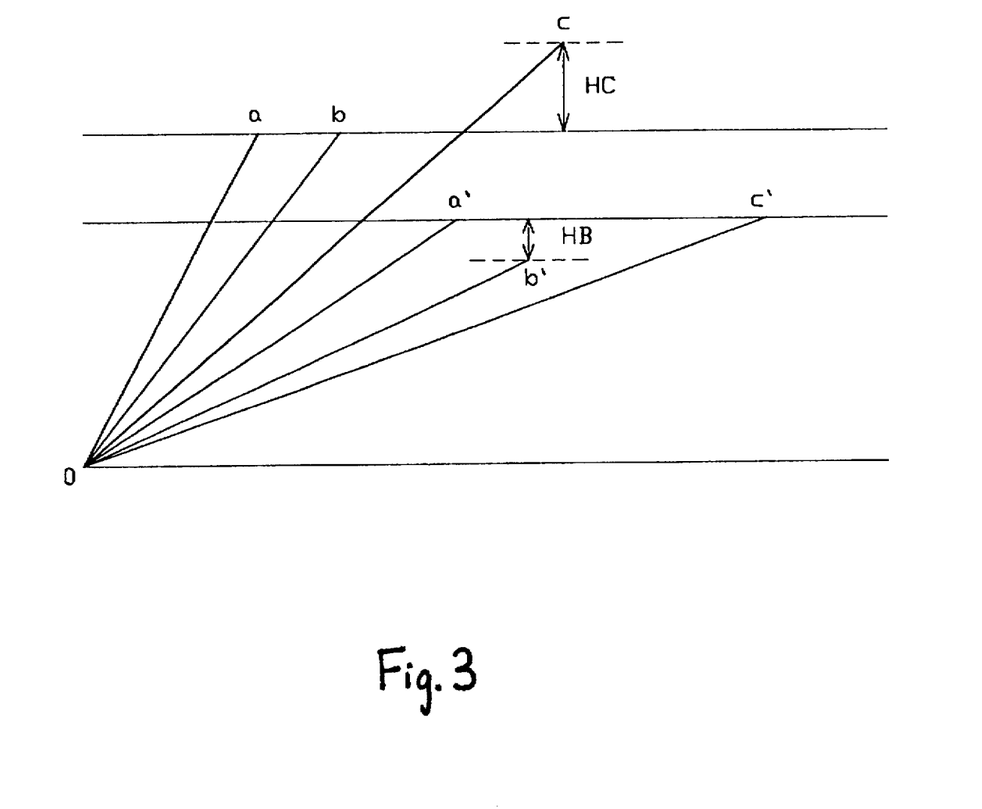
FIG. 3 is a view of the projections of the three points on plane V, illustrating the principle of similar triangles utilized by the present invention.

In FIG. 3, points a, b are originally at equal height and point c is different from point a (or b) in height by positive Hc. The lower joint is used to adjust points a, c by an amount equal to positive Hc. The lower joint is used to adjust points a, c to be at equal height. At this time, point b becomes longer than points a, c by Hb, and Hc>>Hb.

Figure 4:
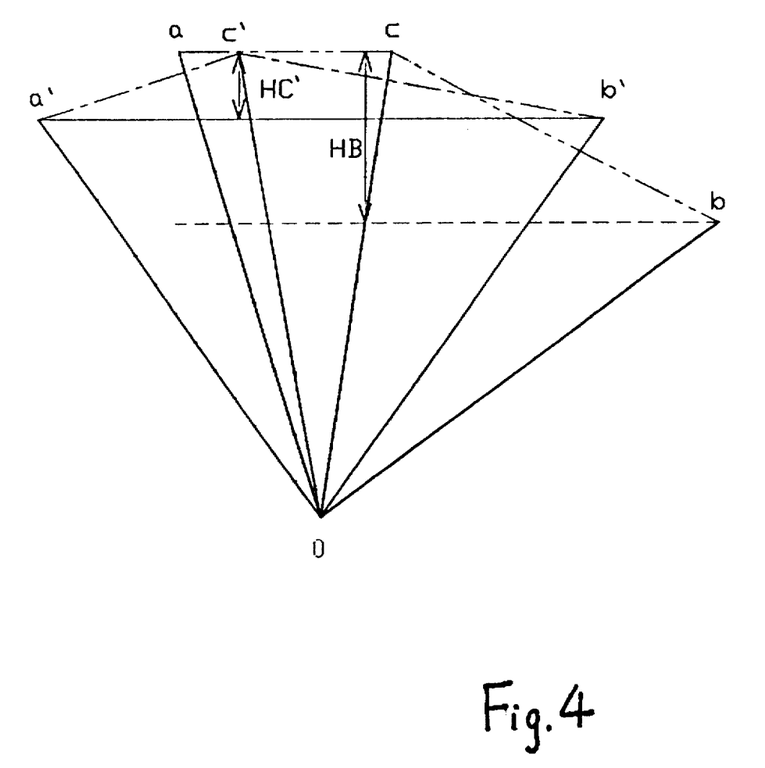
FIG. 4 is a view of the projections of the three points on plane P, illustrating the principle of similar triangles utilized by the present invention.

In FIG. 4, points a, c are at equal height and point b is lower than points a, c by an amount equal to Hb. When using the upper joint to adjust points a, b to be at equal height, point c becomes higher than point a by an amount Hc' and Hb>>Hc'.

Introducing Hc' to FIG. 3, Hb' can be obtained where Hc'>>Hb'. Therefore, Hc>>Hb>>Hc'>>Hb'>>Hc" ... so that the error is apparently reduced until points a, b, c are at equal height.

Figure 5A:
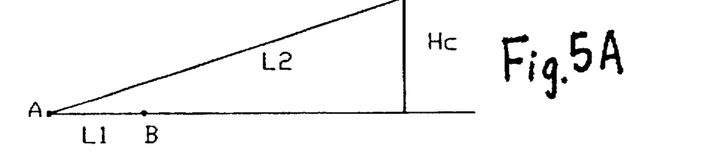
FIGS. 5A to 5D are diagrams demonstrating the principle of similar triangles utilized by the present invention.

The principle of the present method is proved as follows:

Please refer to FIGS. 5A which shows the projections of the three points on plane V prior to adjustment. Because points a, b, c are fixed points on the cast, the spatial relationship between the three points is fixed, that is, no matter how the cast is adjusted and shifted, the relative positions of the three points are constant and irrelevant to the positions of the joints.

Figure 5B:
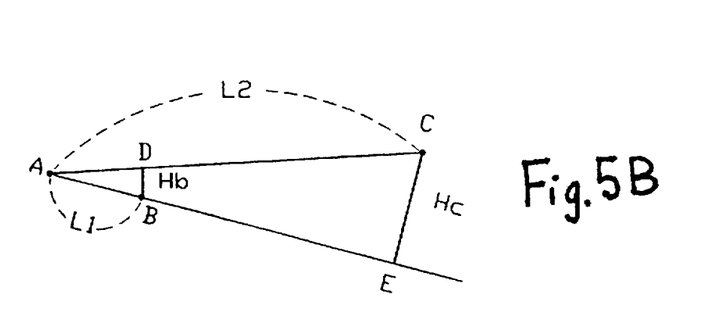

In FIG. 5B, when points a, c are horizontally positioned at equal height, the perpendicular distance from point b to the line created by points a, c is the height difference Hb between point b and points a, c. The height difference Hb can be calculated by means of the principle of similar triangles in geometry:

ABD~ACE are similar triangles so that DB:CE=L1:L2 (Hb) (Hc)

This results in Hb=(L1/L2)*Hc.

Because the height difference between points a, c is Hc, the variation necessary for adjusting points a, c to be at equal height is Hc.

The height difference Hc can be eliminated by rotating the triangle C-A-B about point a or c.

For example, the triangle C-A-B can be rotated about point a with line AC=L2 and line AB=L1. The height variation of point b is L1/L2 times that of point c, that is, the ratio of the radius of rotation. Therefore, the total variation is given by: Hb=(L1/L2)*Hc (formula 1).

Figure 5C:
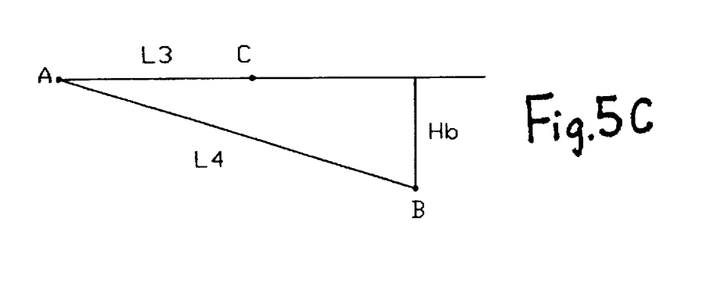
Figure 5D:
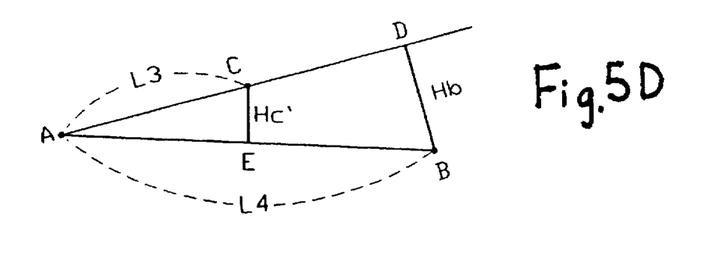

Referring to FIGS. 5C and 5D, which respectively show the projections of the three points on plane P prior to and after adjustment, the principle can thus be proved on plane V as follows:

ABD~ACE are similar triangles so that DB:CE=L4:L3 (Hb) (Hc')

This results in Hc'=(L3/L4)*Hb.

By substituting formula 1 in the above formula, one finds that Hc'=(L3/L4)*(L1/L2)*Hc.

Therefore, the reduction of error is as follows:

$$\frac{Hc'}{Hc} = (L3/L4) * (L1/L2)$$

In conclusion, after points a, c are adjusted to be at equal height, points a, b are again adjusted to be at equal height. The accuracy of this method is significantly greater than that of conventional methods and the error is reduced to be (L1/L2)*(L3/L4) times the original error.

For example, after the first round of adjustment of points a, c and adjustment of points a, b, the reduction of error is (L1/L2), (L3/L4). After the second round of adjustment of points a, c and adjustment of points a, b, the reduction of error is {(L1/L2)*(L3/L4)}². After the third round of adjustment of points a, c and adjustment of points a, b, the reduction of error is {(L1/L2)*(L3/L4)}³.

Therefore, each additional round or cycle of adjustment will reduce the error by a factor of (L1/L2)*(L3/L4).

SUMMARY OF THE INVENTION

It is therefore a primary object of the present invention to provide a method and an apparatus of recording and reproducing the path of insertion of a cast on a dental surveyor. The method uses the principle of similar triangle in geometry. In practical operation, only three steps are required for causing the three points to be equal heights with an error much less than that can be visually conceived: 1. causing points a, b to be at equal eight; 2. causing points a, c to be at equal height; and 3. again causing points a, b to be at equal height. The steps can be repeated to more quickly, conveniently and precisely make the three points be at an equal height. For each additional round of the above steps, the error is reduced by one iteration of (L1/L2)*(L3/L4).

It is a further object of the present invention to provide a method as described above, in which case that the cast is placed on a cast mounting platform that has an irregular non-planar profile or even has an irregular nonplanar base, the three points can be still easily adjusted to be at equal heights without trouble.

The present invention can be best understood through the following description and accompanying drawings, wherein:

DETAILED DESCRIPTION OF THE PREFERRED EMBODIMENT

Figure 1:
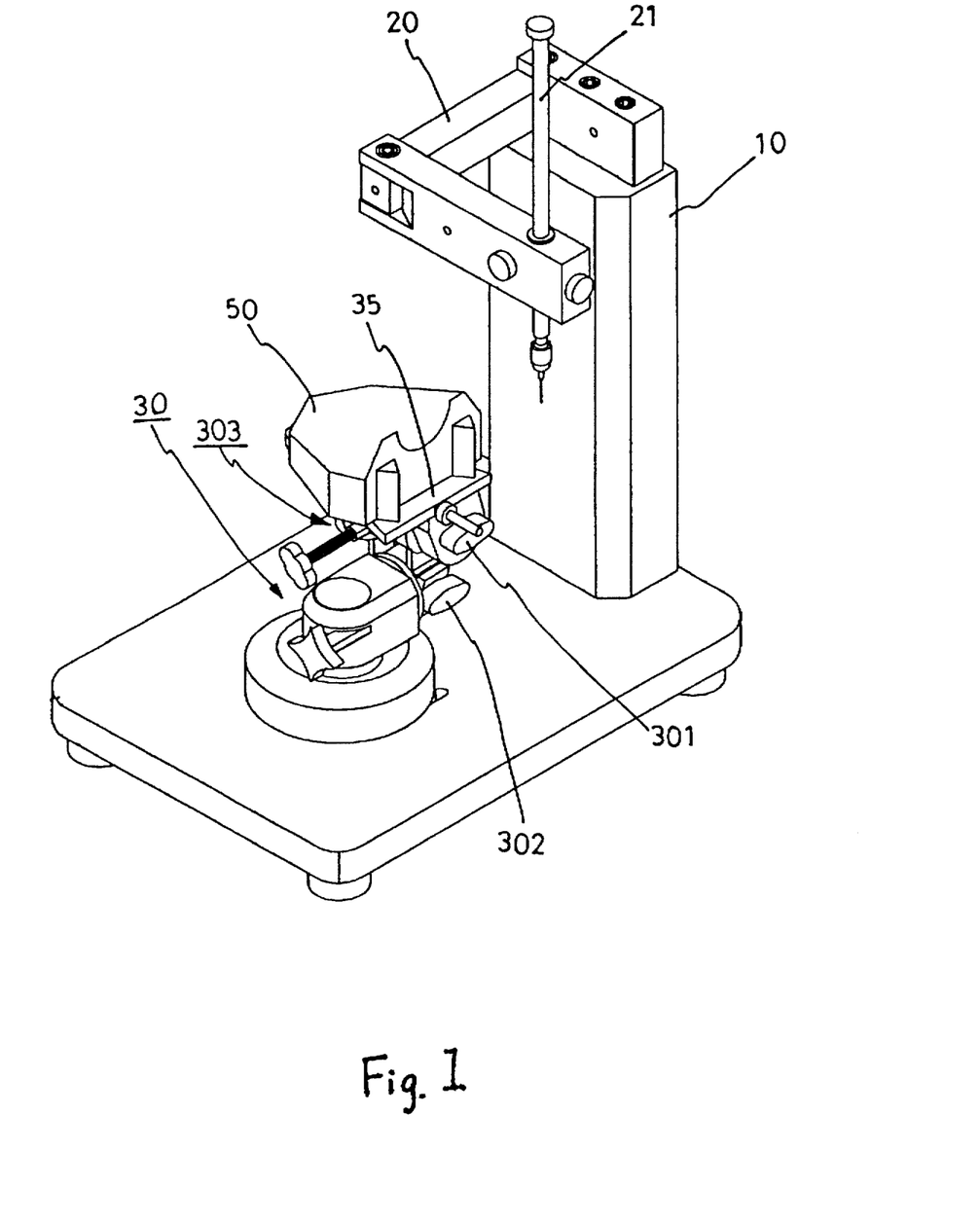
FIG. 1 is a perspective assembled view of the surveyor of the present invention.

Please refer to FIG. 1. In the "interapproaching method" of the present invention, the surveyor table 30 disclosed in the original application is still utilized, this table includes upper and a lower joints 301, 302 and a rotation adjustment 303. When using the present method to adjust the three points a, b, c on the cast 50 to be at equal height, by means of controlling the shifting direction of the cast 50, the two points other than the adjusted one are shifted to be nearly at equal height. During the shifting procedure, the slight error is quickly corrected until the three points are at equal height according to the principle of iteration so as to locate the three points.

Figure 6:
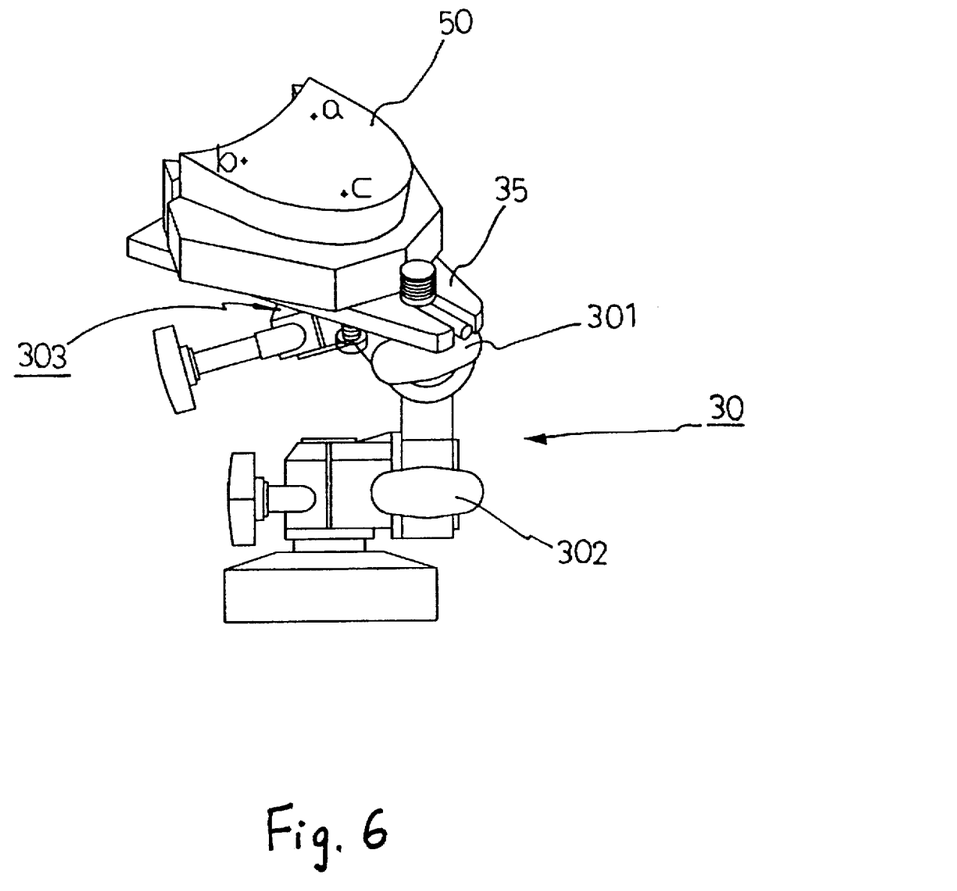
FIG. 6 is a view showing a cast that has been placed on the surveyor table prior to adjustment.

The operation steps of the "iteration method" of the present invention are as follows:

1. The cast 50 is placed and secured on the cast mounting platform 35 of the surveyor table 30. The spatial relationship between the three points a, b, c is as shown in FIG. 6.

Figure 7A:
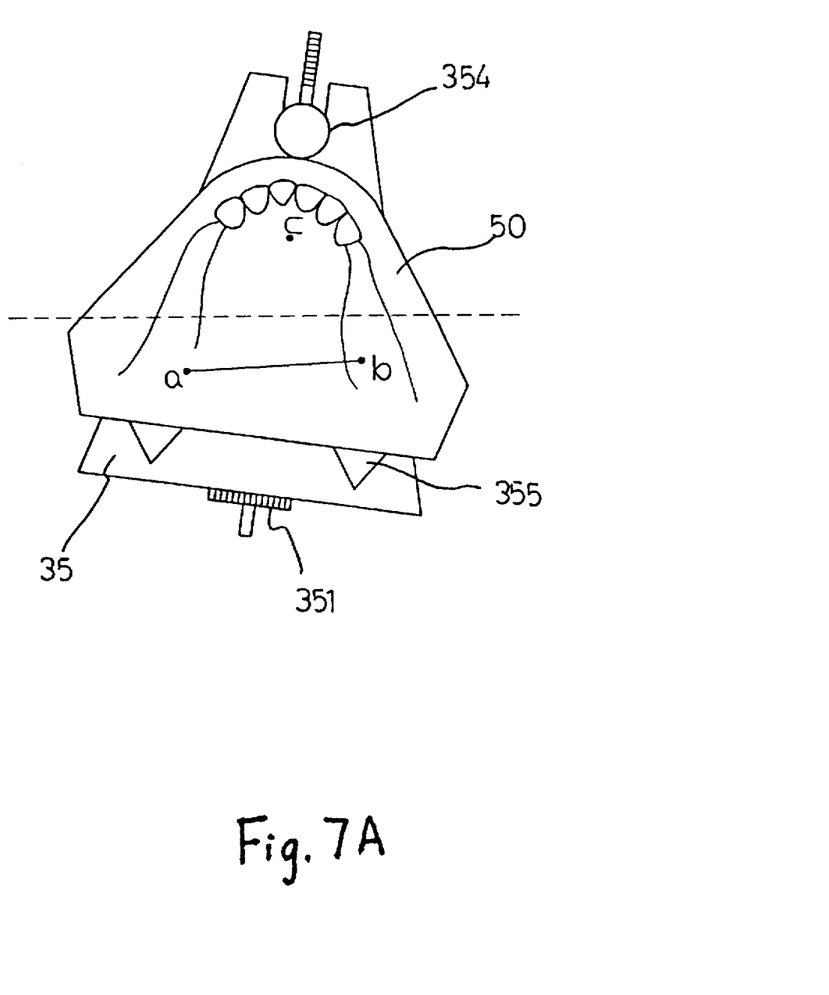
FIG. 7A is a view of the projection of the cast on plane H, in which the line created by points a, b is adjusted to be parallel to the long axis of the lower joint (represented by the phantom line)
Figure 7B:
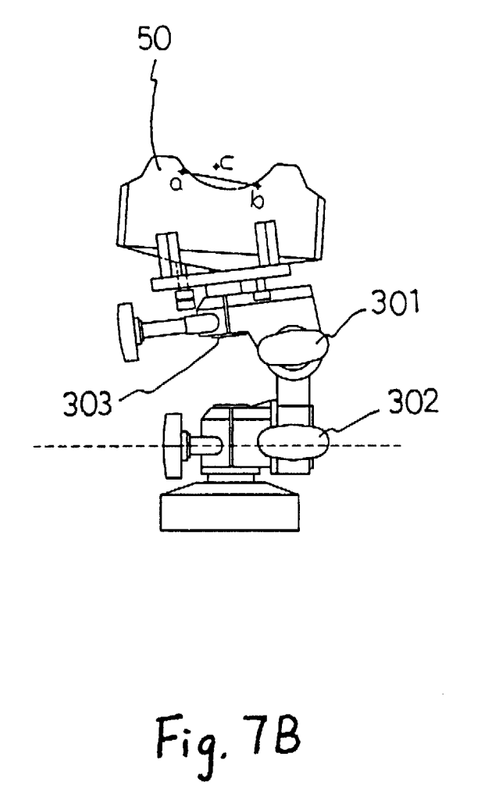
FIG. 7B is a view of the projection of the cast on plane P, in which points a, b are not yet at equal height.

2. Referring to FIGS. 7A and 7B and FIG. 2, by means of the rotation adjustment 303, the line created by the two points a, b is adjusted to be as parallel to the long axis of the lower (or upper) joint 302 as possible.

Figure 8:
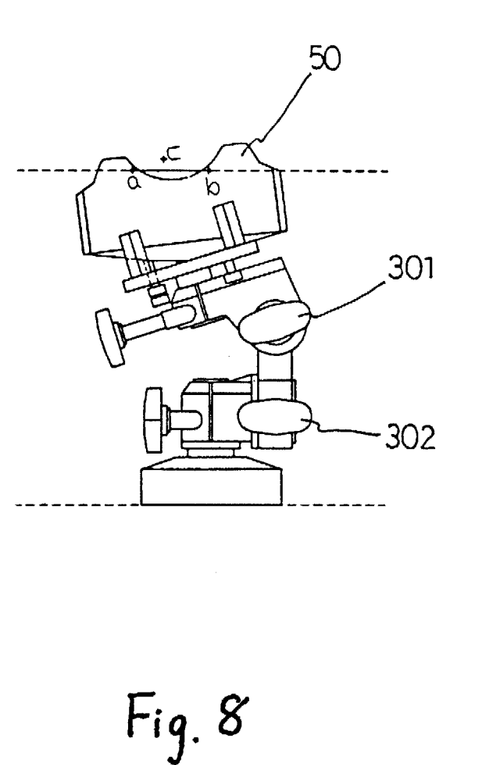
FIG. 8 is a view of the projection of the cast on plane P, in which the upper joint is used to adjust points a, b to be at an equal height.
Figure 9:
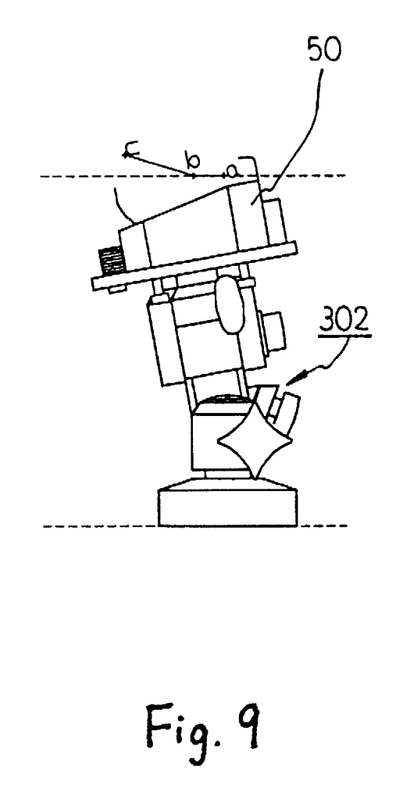
FIG. 9 is a view of the projection of the cast on plane V, in which points a, b are at equal height prior to adjustment of points a, c.

3. As shown in FIG. 8, by means of adjustment of the upper (or lower) joint 301 and the surveying of the vertical spindle 21 of the horizontal arm 20, the two points a, b are caused to be at an equal height. At this time, as may be seen from FIG. 8, point c is not at an equal height to points a, b, but instead is at a height difference of Hc. This is more clearly seen from FIG. 9 which is a view of 90 degrees rotated surveyor of FIG. 8.

Figure 10:
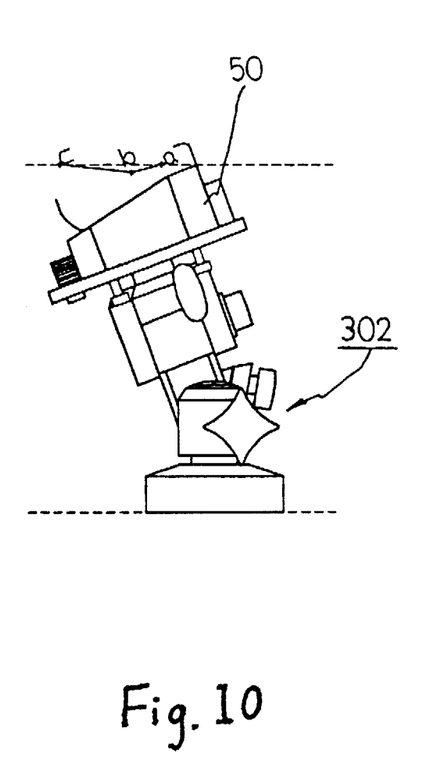
FIG. 10 is a view according to FIG. 9, in which the lower joint is used to adjust points a, c to be at an equal height.

4. Referring to FIGS. 10 and 3, the lower (or upper) joint 302 is used to adjust points a, c to be at equal height. At this time, point b is not at equal height to points a, c with a height difference of Hb.

5. Referring to FIGS. 8 and 4, the upper (or lower) joint 301 is further used to adjust points a, b to be at equal height. At this time, point c is not at equal height to points a, b with a height difference of Hc'.

The formula for the deviation is provided by the aforesaid proof of the principle of the present method namely:

$$Hc' = (L1/L2)*(L3/L4)*Hc$$

Therefore, the above steps 4 and 5 can be repeated to use the upper and lower joints for interadjusting the positions of points a, b, c so as to quickly and conveniently make the three points at be an equal height. Accordingly, each additional round or cycle of steps 4 and 5 will make the error further reduce the error by one involution of $(L1/L2)*(L3/L4)$. In practical operation, only three steps are required for making the three points be at equal height with an error much less than that can be visually conceived: 1. causing points a, b to be at equal height; 2. causing points a, c to be at equal height; and 3. again causing points a, b to be at equal height. The above method can be performed more conveniently, quickly and precisely than any conventional method.

In conclusion, the advantages of the interapproaching method of the present invention are as follows:

1. The steps of operation are simple and easy.
2. The error between the height of the three points can be quickly reduced.
3. It is no longer necessary to adjust the screw as in a conventional operation.
4. A cast with a very regular plane base is no longer needed.

The above embodiment is only an example of the present invention and the scope of the present invention should not be limited to the example. Any modification or variation derived from the example should fall within the scope of the present invention.

What is claimed is:

1. A method for recording and reproducing a path of insertion of a cast on a dental surveyor, said cast being secured on a cast mounting platform situated on a surveyor table, said surveyor table being mounted for rotation about a spindle, an orientation of said spindle and table being adjustable by means of two pivotable arms, one of which extends generally horizontally and the other of which extends generally vertically, said cast including three points a, b, and c whose positions are to be adjusted to be of equal height, comprising the steps of:

(a) rotating the table about the spindle until a line connecting points a and b is as parallel to a long axis of the generally horizontally extending arm as possible;
   (b) pivoting the generally vertically extending arm until points a and b are at an equal height;
   (c) pivoting the generally horizontal arm until points a and c are at an equal height;
   (d) repeating steps (b) and (c) until points a, b, and c are all at an equal height.

2. A method as claimed in claim 1, wherein a height difference Hc' between point c and points a and b after step (d) has been carried out by repeating step (b) is given by the formula Hc'=(L1/L2)*(L3/L4)*Hc, where Hc is the height difference between point c and points a and b after step (b) has been carried out, L1 is a length between projections of points a and b on a first plane, L2 is a length between projections of points a and c on said first plane, L3 is a length between projections of points a and c on a second plane, and L4 is a length between projections of points a and b on the second plane; and wherein a height difference between point b and points c and a after step (c) has been carried out is related to Hc and Hc' by the formulas Hb=(L1/L2)*Hc and (L3/L4)*Hb=Hc'.

3. Apparatus for recording and reproducing a path of insertion of a cast on a dental surveyor, said cast being secured on a cast mounting platform, comprising: a surveyor table on which said cast mounting platform is situated and which is mounted for rotation about a spindle, an orientation of said spindle and table being adjustable by means of two pivotable arms, one of which extends generally horizontally and the other of which extends generally vertically, said cast including three points a, b, and c whose positions are to be adjusted to be of equal height;

means for enabling rotation of the surveyor table about the spindle until a line connecting points a and b is as parallel to a long axis of the generally horizontally extending arm as possible;

means for enabling pivoting of the generally vertically extending arm until points a and b are at an equal height; and means for enabling pivoting of the generally horizontal arm until points a and c are at an equal height, whereby said pivot means are arranged to enable alternative adjustment of the heights of points a,b and b,c until points a, b, and c are all at an equal height.

* * * * *